United States Patent  (10) Patent No.: US 7,514,455 B2
Omura et al.  (45) Date of Patent: Apr. 7, 2009

(54) INHIBITORS AGAINST COMPLEX II OF ELECTRON TRANSPORT SYSTEM

(75) Inventors: Satoshi Omura, Tokyo (JP); Kazuro Shiomi, Tokyo (JP); Hiroshi Tomoda, Tokyo (JP); Rokuro Masuma, Tokyo (JP); Kiyoshi Kita, Tokyo (JP)

(73) Assignee: The Kitasato Institute, Tokyo (JP)

( * ) Notice: Subject to any disclaimer, the term of this patent is extended or adjusted under 35 U.S.C. 154(b) by 664 days.

(21) Appl. No.: 10/489,964

(22) PCT Filed: Jun. 10, 2002

(86) PCT No.: PCT/JP02/05727

§ 371 (c)(1), (2), (4) Date: Aug. 17, 2004

(87) PCT Pub. No.: WO03/103667

PCT Pub. Date: Dec. 18, 2003

(65) Prior Publication Data

US 2004/0266835 A1 Dec. 30, 2004

(51) Int. Cl.
C07D 211/84 (2006.01)
A61K 31/4415 (2006.01)

(52) U.S. Cl. .................. 514/350; 546/296
(58) Field of Classification Search ............... None
See application file for complete search history.

(56) References Cited

FOREIGN PATENT DOCUMENTS

JP 50-132183 10/1975
JP 5-339156 12/1993

OTHER PUBLICATIONS

Takashi Kanamori and Shigeo Ohta, "Electron Transport System and Energy Converting System", Kyoritsu Shuppan, 2001, pp. 9-13.
Kozo Utsumi, "List of inhibitors used for studies on energy transduction of mitochondria", Kyoritsu Shuppan, 2001, pp. 425-426. (p. 425, Table 1 in English).
Yasuo Kagawa and Akira Asano, Preparative Methods for Mitochondria and Compositional Components, Tokyo Kagaku Dozin, 1976, pp. 216-255. (p. 249, Table 7-6 in English).
Oshino, K.; Kumagai, H.; Tomoda, H.; Omura, S., Mechanism of action of atpenin B on Raji Cells. J. Antibiot., 1990, vol. 43, No. 9, pp. 1064 to 1068.
Kumagai, H.; Nishida, H.; Imamura, N.; Tdomoda, H.; Omura, S.; Bordner, J., The structures of atpenins A4, A5 and B, new antifungal antibiotics produced by *Penicillium* sp. J. Antibiot., 1990, vol. 43, No. 12, pp. 1553 to 1558.
Cutler, H.G.; Jacyno, J.M. Biological activity of (−)-harzianopyridone isolated from *Trichoderma harzianum*. Agric. Biol. Chem., 1991, vol. 55, No. 10, pp. 2629 to 2631.
S. Takamiya et al., Developmental changes in the respiratory chain of *Ascaris* mitochondria, Biochimica et Biophysica Acta, 1141 (1993) 65-75.
F. Trecourt et al., First Synthesis of (±)-Harzianopyridone by Metalation of Polysubstituted O-Pyridylcarbamates, pp. 1117-1124, 1995.
S. Omura et al., Atpenins, New Antifungal Antibiotics Produced by *Penicillium* SP., The Journal of Antibiotics, vol. XLI No. 12, pp. 1769-1773, 1988.
J.M. Dickinson et al., Structure and Biosynthesis of Harzianopyridone, an Antifungal Metabolite of *Trichoderma harzianum*, J. Chem. Soc. Perkin Trans. I 1989, pp. 1885-1889.
F. Saruta et al., Stage-specific Isoforms of Complex II (Succinate-Ubiquinone Oxidoreductase) in Mitochondria from the Parasitic Nematode, *Ascaris Suum*, The Journal of Biological Chemistry, vol. 270, No. 2, Issue of Jan. 13, pp. 928-932, 1995.
P.C. Mowery et al., Carboxins: Powerful Selective Inhibitors of Succinate Oxidation in Animal Tissues, Biochemical and Biophysical Research Communications, vol. 71, No. 1, 1976, pp. 354-361.

*Primary Examiner*—Zinna N Davis
(74) *Attorney, Agent, or Firm*—Young & Thompson

(57) ABSTRACT

An electron transport system complex II inhibitor comprising 2-pyridinol derivative represented by the general formula [I]

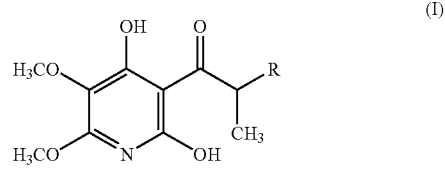

(I)

wherein R is alkyl or alkenyl optionally having substituent containing halogen, or its tautomer 2-pyridone derivative represented by the general formula [II]

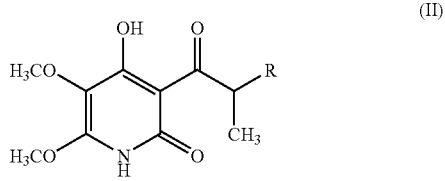

(II)

wherein R is alkyl or alkenyl optionally having substituent containing halogen, or salt thereof as an active ingredient. The compound inhibits the complex II strongly with nM order activity. Consequently, 2-pyridinol derivative or its tautomer, 2-pyridone derivative, are useful as the complex II inhibitor.

10 Claims, No Drawings

INHIBITORS AGAINST COMPLEX II OF ELECTRON TRANSPORT SYSTEM

DESCRIPTION

This application is a 371 of PCT/JP02/05727 filed Jun. 10, 2002.

TECHNICAL FIELD

The present invention relates to, for example, a protein complex involved in the electron transport system responsible for oxidative phosphorylation for synthesis of adenosine triphosphate (ATP) in mitochondria. More particular, the present invention relates to the inhibitors of electron transport system complex II (succinate-ubiquinone oxidoreductase).

BACKGROUND ART

In the electron transport system responsible for the oxidative phosphorylation for synthesis of ATP in mitochondria, mainly four types of protein complexes are involved, and are called as complexes I, II, III and IV (Kozo Utsumi and Masayasu Inoue, Ed. "New Mitochondriology" pages 8-13; Takashi Kanamori and Shigeo Ohta, "Electron Transport System and Energy Converting SyStem", Kyoritsu Shuppan. 2001). For these complexes, i.e. the complex I (NADH-ubiquinone oxidoreductase), the complex III (ubiquinol-cytochrome c oxidoreductase), and the complex IV (cytochrome c oxidoreductase), superior inhibitors have been known and are used in the biochemical studies (Kozo Utsumi and Masayasu Inoue, Ed. "New Mitochondriology", pages 424-426; Kozo Utsumi, "List of inhibitors used for studies on energy transduction of mitochondria", Kyoritsu Shuppan, 2001).

With regard to the complex II (succinate-ubiquinone oxidoreductase) inhibitor, thenoyltrifluoroacetone, etc. has been frequently used, however its inhibitory concentration was very weak such as in the order of iM (The Japanese Biochemical Society, Ed., Experimental Biochemistry, No. 12, "Energy Metabolism and Biological oxidation" (Upper volume) pages, 215-255; Yasuo Kagawa and Akira Asano, "Preparative Methods for Mitochondria and Compositional Components, Tokyo Kagaku Dozin, 1976). Further, carboxins have been said to have strongest inhibitory activity among the prior known complex II inhibitors (P. C. Mowery, B. A. C. Ackrell and T. P. Singer, Biochem. Biophys. Res. Commun., 71, 354-361, 1976), however, it was considerably weak activity as compared with rotenone, a complex I inhibitor, and antimycin, a complex III inhibitor (The Japanese Biochemical Society, Ed. Experimental Biochemistry, No. 12, "Energy Metabolism and Biological Oxidation" (Upper volume) pages, 215-255; Yasuo Kagawa and Akira Asano, "Preparative Methods for Mitochondria and Compositional Components, Tokyo Kagaku Dozin, 1976).

DISCLOSURE OF THE INVENTION

We have explored superior inhibitors against electron transport system, the complex II. As a result, we have found unexpectedly the superior inhibitory activities against the complex II in the known antibiotics atpenin A4, atpenin A5, atpenin B and harzianopyridone, which are 2-pyridinol derivatives or tautomers 2-pyridone derivatives, and completed the present invention.

The present invention has been completed by the knowledge hereinabove. Accordingly, an object of the present invention is to provide the electron transport system complex II inhibitor, which has extremely higher inhibitory activity than the known complex II inhibitors such as thenoyltrifluoroacetone and carboxins and advantageously used for studies on biochemistry.

The present invention relates to the electron transport system complex II inhibitor comprising a compound selected from the group consisting of 2-pyridinol derivative represented by the general formula [I]

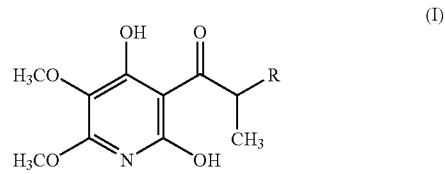

wherein R is alkyl or alkenyl optionally having substituents containing halogen, or its tautomer 2-pyridone derivative of the general formula [II]

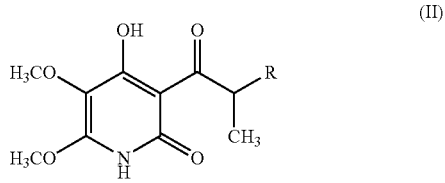

wherein R is alkyl or alkenyl optionally having substituents containing halogen, or salt thereof, as an active ingredient.

Examples of alkyl group are, for example, methyl, ethyl, propyl, isopropyl, butyl, isobutyl, pentyl, isopentyl, 2-methylbutyl, hexyl, 2-methylpentyl, 3-methylpentyl, 4-methylpentyl, 2-ethylbutyl, heptyl, octyl, etc. Examples of alkenyl are, for example, 1-propenyl, allyl, 1-butenyl, 2-butenyl, 1-pentenyl, 2-pentenyl, 3-pentenyl, 3-methyl-2-butenyl, geranyl, etc.

The present invention, further, relates to the electron transport system complex II inhibitor, atpenin A4 represented by the formula [III]

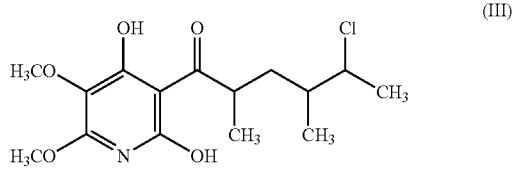

Such the inhibitor is the electron transport system complex II inhibitor having inhibitory activity against any of bovine heart complex II, rat liver complex II and *Ascaris suum* complex II.

The present invention, further, relates to the electron transport system complex II inhibitor, atpenin A5 represented by the formula [IV]

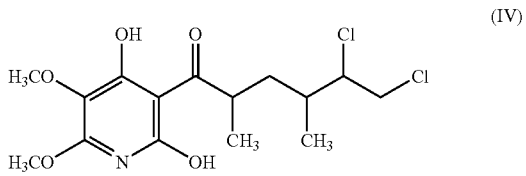

Such the inhibitor is the electron transport system complex II inhibitor having inhibitory activity against any of bovine heart complex II, rat liver complex II and *Ascaris suum* complex II.

The present invention, further, relates to the electron transport system complex II inhibitor, atpenin B represented by the formula [V]

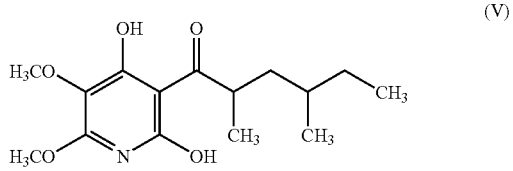

Such the inhibitor is the electron transport system complex II inhibitor having inhibitory activity against any of bovine heart complex II, rat liver complex II and *Ascaris suum* complex II.

The present invention, further, relates to the electron transport system complex II inhibitor, harzianopyridone represented by the formula [VI]

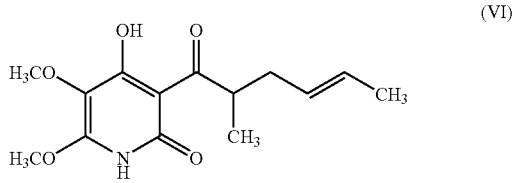

Such the inhibitor is the electron transport system complex II inhibitor having inhibitory activity against any of bovine heart complex II, rat liver complex II and *Ascaris suum* complex II.

The present invention is further relates to a microorganism, which produces atpenin A4 represented by the formula [III], atpenin A5 represented by the formula [IV] and atpenin B represented by the formula [V], hereinbefore having inhibitory activity against the electron transport system complex II, is *Penicillium* sp. FO-125 FERM BP-8084.

The known antibiotics-atpenin A4, atpenin A5 and atpenin B used in the present invention are antifungal antibiotics, which were found by two of inventors of the present invention, Satoshi Omura and Hiroshi Tomoda, in the culture medium of a strain, *Penicillium* sp. FO-125, as having antifungal activity, and were designated as FO-125A4, A5 and B, and filed the patent application (JP, H01-199582, A). Consequently, the present substances, atpenins A4, A5 and B can be obtained by the method described in JP, H01-199582, A or its modification, i.e. culturing *Penicillium* sp FO-125 strain and purifying the cultured liquid thereof.

Seed culture of the present strain is cultured in the jar fermenter, and the cultured liquid is centrifuged to obtain supernatant. The supernatant is extracted with ethyl acetate, concentrated and subjected to silica gel column chromatography, then eluted with hexane-ethyl acetate. The thus obtained crude substance of atpenins is treated by Sephadex LH-20 column chromatography, eluted with chloroform-methanol to obtain purified atpenin A4, A5 and B. The purified atpenins A4, A5 and B can also be obtained by once or repeated reverse phase high performance liquid chromatography using acetonitrile containing 10 mM phosphate buffer (pH 3.0).

The above atpenins A4, A5 and B producing strain *Penicillium* sp. FO-125 strain were deposited according to the Budapest Treaty on the International Recognition of the Deposit of Microorganisms for the Purpose of Patent Procedure in International Patent Organism Depositary, National Institute of Advanced Industrial Science and Technology, of AIST Tsukuba Central 6, 1-1, Higashi 1-Chome Tsukuba-shi, Ibaraki-ken 305-8566 Japan, on May 22, 2002, and given a permanent deposition No. FERM BP-8048.

Taxonomical properties of the strain *Penicillium* sp. FO-125 are described in JP, H01-199582, A, however the present strain is the re-deposited strain and the taxonomical properties thereof are explained hereinbelow.

(a) Morphological Properties

The strain showed good growth on malt-extract agar, potato glucose agar, YpSs agar, etc. with good bearing of conidia. Microscopic observation of colonies grown on YpSs medium showed transparent hyphae with septa and direct growth of conidiophore from basal mycelia.

Penicillus is biverticillate-symmetric. Sizes are full of varieties with rarely monoverticillate. Size of metula is 15-20× 3-4 im with bearing 3-5 metulae. Form of metula is a nib grown with 3-6, size 10-15×2-4 im.

At first, a phialoconidium is born on the top of the sterigma, and is linked depending on time, and finally the linkage is about 150 im in length. Electron microscopic observation shows ellipsoidal conidium with size of 2.2-3.1×1.6-2.0 im and surface is smooth.

(b) Properties on Various Media

Macroscopic observation of the strain cultured on various media at 27° C. for 14 days are shown in Table 1.

TABLE 1

| Medium Growth on medium | Color tone of reverse of colony | Conidium Formation | Conidium Color | Soluble pigment | Diameter of colony |
|---|---|---|---|---|---|
| Malt extract agar Good, no diffusion of hyphae, velvety, white | Penumbra: yellowish green Center: dark red brown | Good | Yellowish green-green | None | 58 mm |
| Potato-glucose agar Good, no diffusion of hyphae, velvety, white | yellowish green | Good | Green | None | 60 mm |
| Czapek agar Good, no diffusion of hyphae, felty, white | Ivory | Medium | Ivory | None | 62 mm |

TABLE 1-continued

| Medium Growth on medium | Color tone of reverse of colony | Conidium Formation | Conidium Color | Soluble pigment | Diameter of colony |
|---|---|---|---|---|---|
| Sabouraud agar Good, no diffusion of hyphae, felty, white | Beige | Good | Pale blue | None | 61 mm |
| Oatmeal agar Good, Growth with diffusion of hyphae, velvety, white | Yellow-yellowish green | Good | Deep green | None | 65 mm |
| Synthetic mucor agar Good, Growth with long diffusion of hyphae, wooly, transparent | Colorless | Slightly bearing | White | None | 66 mm |
| YpSs agar Good, no diffusion of hyphae, velvety, white | White-green | Good | Green | None | 64 mm |

(c) Physiological and Ecological Properties

Optimum growth condition of the present strain is pH 4-8 at 22-33° C. in YpSs medium. Growth range of this strain is pH 2-9 at 15-39° C. in YpSs medium. The strain is aerobic microorganism.

Physico-chemical properties of atpenin A4, atpenin A5 and atpenin B obtained from the strain of *Penicillium* sp. FO-125 having properties hereinabove described were identical with those described in the references (S. Omura, et al. J. Antibiot., 41, 1769-1773, 1988 and H. Kumagai, et al. ibid. 43, 1553-1558, 1990).

Physico-chemical properties of the present substance, atpenins A4, A5 and B are summarized as follows.

[Atpenin A4]

(1) Nature: white powder
(2) Molecular weight: 331
(3) Molecular formula: $C_{15}H_{22}NO_5Cl$
(4) UV absorption (in ethanol): maximum absorption at 235 nm, 267 nm and 320 nm.
(5) IR absorption (KBr tablet): maximum absorption at 1645, 1600, 1440, 1320, 1200, 1160 and 995 cm$^{-1}$.
(6) $^1$H NMR spectrum, chemical shift (ppm) in deuterated chloroform and J: coupling constant (Hz): ä4.19 (3H, s), 4.18 (1H, m), 4.14 (1H, dq, J=3.1, 6.7), 3.80 (3H, s), 1.82 (1H, m), 1.76 (1H, m), 1.53 (1H, ddd, J=6.2, 6.2, 12.4), 1.45 (3H, d, J=6.7), 1.15 (3H, d, J=6.8), 0.96 (3H, d, J=6.7).
(7) $^{13}$C NMR spectrum, chemical shift (ppm) in deuterated chloroform: ä 210.1, 171.1, 161.8, 155.5, 121.2, 100.5, 63.1, 61.5, 57.9, 39.9, 37.7, 37.1, 22.7, 17.7, 14.1.

From the above described physico-chemical properties and spectral data, atpenin A4 was analyzed to have the chemical structure as shown in the formula [III] hereinbelow.

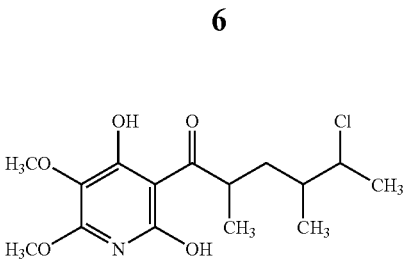

(III)

[Atpenin A5]

(1) Nature: white powder
(2) Molecular weight: 365
(3) Molecular formula: $C_{15}H_{21}NO_5Cl_2$
(4) UV absorption (in ethanol): maximum absorption at 237 nm, 272 nm and 320 nm.
(5) IR absorption (KBr tablet): maximum absorption at 1645, 1600, 1440, 1320, 1200, 1160 and 995 cm$^{-1}$.
(6) $^1$H NMR spectrum, chemical shift (ppm) in deuterated chloroform and J: coupling constant (Hz): ä4.21 (3H, s), 4.21 (1H, m), 4.11 (1H, ddd, J=2.6, 5.9, 8.5), 3.77 (3H, s), 3.71 (1H, dd, J=5.9, 11.2), 3.62 (1H, dd, J=8.5, 11.2), 2.16 (1H, m), 1.90 (1H, ddd, J=7.1, 8.1, 13.6), 1.50 (1H, ddd, J=6.5, 7.3, 13.6), 1.15 (3H, d, J=6.8), 0.92 (3H, d, J=6.5).
(7) $^{13}$C NMR spectrum, chemical shift (ppm) in deuterated chloroform: ä209.8, 172.5, 161.9, 155.2, 120.9, 100.8, 65.4, 61.6, 58.3, 45.9, 39.3, 37.5, 32.5, 18.0, 12.9.

From the above described physico-chemical properties and spectral data, atpenin A5 was analyzed to have the chemical structure as shown in the formula [IV] hereinbelow.

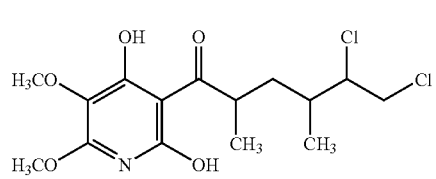

(IV)

[Atpenin B]

(1) Nature: white powder
(2) Molecular weight: 297
(3) Molecular formula: $C_{15}H_{23}NO_5$
(4) UV absorption (in ethanol): maximum absorption at 237 nm, 270 nm and 318 nm.
(5) IR absorption (KBr tablet): maximum absorption at 1645, 1600, 1440, 1320, 1200, 1160 and 995 cm$^{-1}$.
(6) $^1$H NMR spectrum, chemical shift (ppm) in deuterated chloroform and J: coupling constant (Hz): ä4.30 (1H, m), 3.78 (3H, s), 3.71 (3H, s), 1.71 (1H, ddd, J=5.3, 5.9, 12.5), 1.38 (1H, m), 1.33 (1H, m), 1.21 (1H, m), 1.19 (3H, d, J=6.6), 1.06 (1H, m), 0.71 (3H, dd, J=7.3, 7.3), 0.86 (3H, d, J=6.4).
(7) $^{13}$C NMR spectrum, chemical shift (ppm) in deuterated chloroform: ä211.7, 165.8, 162.6, 159.9, 124.9, 100.6, 60.6, 54.3, 41.9, 41.1, 30.6, 21.0, 19.1, 17.1, 11.7.

From the above described physico-chemical properties and spectral data, atpenin B was analyzed to have the chemical structure as shown in the formula [V] hereinbelow.

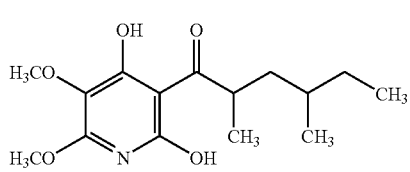

(V)

[Harzianopyridone]

Harzianopyridone can be synthesized according to the description of F. Trecourt, et al., J. Heterocyclic Chem., 32, 1117-1124, 1995 as follows. 6-Bromo-2,3-dimethoxy-N,N-disiopropylcarbamate was obtained by four steps of synthesis from 2,3-dimethoxypyridine, and was converted to pyridone, which was protected with (2-(trimethylsilyl)ethoxy)methyl group. Butyl lithium was added thereto and the reaction mixture was reacted with (4E)-2-methyl-4-hexenal to obtain alcohol, which was oxidized by pyridinium chlorochromate to ketone, subsequently deprotected the carbamate and SEM to synthesize harzianopyridone. Physico-chemical properties of the thus obtained harzianopyridone were identical with those described in the reference (Julia, M. et al. J. Chem. Soc. Perkin Trans. 1, 1885-1887, 1989).

Physico-chemical properties of harzianopyridone are summarized as follows.

(1) Nature: white powder
(2) Molecular weight: 281
(3) Molecular formula: $C_{14}H_{19}NO_5$
(4) UV absorption (in ethanol): maximum absorption at 243 nm, 267 nm and 331 nm.
(5) IR absorption (KBr tablet): maximum absorption at 1725, 1650, 1600 and 720 $cm^{-1}$.
(6) $^1H$ NMR spectrum, chemical shift (ppm) in deuterated chloroform and J: coupling constant (Hz): ä16.4 (1H, s), 12.3 (1H, br. s), 5.42 (1H, m), 5.38 (1H, m), 4.17 (3H, s), 3.95 (1H, m), 3.79 (3H, s), 2.45 (1H, ddd, J=6.0, 6.0, 14.5), 2.05 (1H, ddd, J=6.5, 6.5, 14.5), 1.65 (3H, d, J=6.5), 1.30 (3H, d, J=6.5).
(7) $^{13}C$ NMR spectrum, chemical shift (ppm) in deuterated chloroform: ä209.8, 172.9, 161.8, 155.7, 128.7, 127.1, 121.6, 100.6, 61.5, 57.6, 43.1, 36.1, 17.9, 16.3.

From the above described physico-chemical properties and spectral data, harzianopyridone was analyzed to have the chemical structure as shown in the formula [VI] hereinbelow.

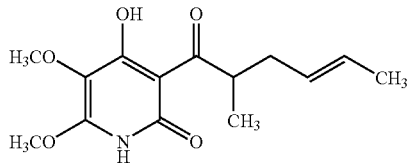

(VI)

BEST MODE FOR CARRYING OUT THE INVENTION

The present invention is explained by mentioning referential examples and examples, but is not construed as limiting these examples.

REFERENTIAL EXAMPLE 1

Inhibitory Activity of Thenoyltrifluoroacetone on Bovine Heart Complex II

With regard to the complex II (succinate-ubiquinone oxidoreductase) of the bovine heart, mitochondria prepared according to the method of S. Takamiya et al. (Developmental changes in the respiratory chain of *Ascaris* mitochondria, Biochim. Biophys. Acta, 1141, 65-71, 1993) were used. Succinate dehydrogenase activity of the complex II was measured by changes of maximum absorption, which was specific to the electron acceptor (DCIP), from oxidized form of 2,6-dichlorophenolindophenol (DCIP, Sigma Inc.) to reduced form with the addition of succinate.

Namely, ubiquinone-2 (Sigma Inc.) and DCIP were added to the level of 100 ìM and 70 ìM, respectively, into 50 mM phosphate buffer (pH 7.5); thenoyltrifluoroacetone was added therein; further the complex II was added thereto; then potassium succinate with final concentration of 10 mM was added; and the reaction was started at 25° C. Reaction rate was measured by that the formation rate of reduced form of DCIP (àmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

REFERENTIAL EXAMPLE 2

Inhibitory Activity of Carboxin on Bovine Heart Complex II

With regard to the complex II of the bovine heart, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); carboxin was added therein; further the complex II was added thereto; then potassium succinate with final concentration of 10 mM was added; and the reaction was started at 25° C. Reaction rate was measured by that the formation rate of reduced form of DCIP (àmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 1

Inhibitory Activity of Atpenin A4 on Bovine Heart Complex II

With regard to the complex II (succinate-ubiquinone oxidoreductase) of the bovine heart, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); atpenin A4 was added therein; further the complex II was added thereto; then potassium succinate with final concentration of 10 mM was added; and the reaction was started at 25° C. Reaction rate was measured by that the formation rate of reduced form of DCIP (åmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 2

Inhibitory Activity of Atpenin A4 on Rat Liver Complex II

With regard to the complex II of the rat liver, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); atpenin A4 was added therein; further the complex II was added thereto; then potassium succinate with final concentration of 10 mM was added; and the reaction was started at 25° C. Reaction rate was measured by that the formation rate of reduced form of DCIP (åmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 3

Inhibitory Activity of Atpenin A4 on *Ascaris suum* Complex II

With regard to the complex II of the *Ascaris suum*, the purified complex II prepared according to the method of F. Saruta et al. [Stage-specific Isoforms of Complex II (Succinate-Ubiquinone Oxidoreductase) in Mitochondria from the Parasitic Nematode, *Ascaris suum*: J. Biol. Chem. 270, 928-932, 1995] was used. Succinate dehydrogenase activity of the complex II was measured by changes of maximum absorption, which was specific to the electron acceptor (DCIP), from oxidized form of DCIP to reduced form with the addition of succinate.

Namely, ubiquinone-2 and DCIP were added to the level of 100 ìM and 70 ìM, respectively, into 50 mM phosphate buffer (pH 7.5); atpenin A4 was added therein; further the complex II was added thereto; then potassium succinate with final concentration of 10 mM was added; and the reaction was started at 25° C. Reaction rate was measured by that the formation rate of reduced form of DCIP (åmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 4

Inhibitory Activity of Atpenin A5 on Bovine Heart Complex II

With regard to the complex II of the bovine heart, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); atpenin A5 was added therein; further the complex II was added thereto; then potassium succinate with final concentration of 10 mM was added; and the reaction was started at 25° C. Reaction rate was measured by that the formation rate of reduced form of DCIP (åmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 5

Inhibitory Activity of Atpenin A5 on Rat Liver Complex II

With regard to the complex II of the rat liver, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); atpenin A5 was added therein; further the complex II was added thereto; then potassium succinate with final concentration of 10 mM was added; and the reaction was started at 25° C. Reaction rate was measured by that the formation rate of reduced form of DCIP (åmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 6

Inhibitory Activity of Atpenin A5 on *Ascaris suum* Complex II

With regard to the complex II of the *Ascaris suum*, the purified complex II prepared according to the same method of example 3 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); atpenin A5 was added therein; further the complex II was added thereto; then potassium succinate with final concentration of 10 mM was added; and the reaction was started at 25° C. Reaction rate was measured by that the formation rate of reduced form of DCIP (åmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 7

Inhibitory Activity of Atpenin B on Bovine Heart Complex II

With regard to the complex II of the bovine heart, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); atpenin B was added therein; further the complex II was added thereto; then potassium succinate with final concentration of 10 mM was added; and the reaction was started at 25° C. Reaction rate was measured by that the formation rate of reduced form of DCIP (àmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 8

Inhibitory Activity of Atpenin B on Rat Liver Complex II

With regard to the complex II of the rat liver, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); atpenin B was added therein; further the complex II was added thereto; then potassium succinate with final concentration of 10 mM was added; and the reaction was started at 25° C. Reaction rate was measured by that the formation rate of reduced form of DCIP (àmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 9

Inhibitory Activity of Atpenin B on *Ascaris suum* Complex II

With regard to the complex II of the *Ascaris suum*, the purified complex II prepared according to the same method of example 3 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); atpenin B was added therein; further the complex II was added thereto; then potassium succinate with final concentration of 10 mM was added; and the reaction was started at 25° C. Reaction rate was measured by that the formation rate of reduced form of DCIP (àmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 10

Inhibitory Activity of Harzianopyridone on Bovine Heart Complex II

With regard to the complex II of the bovine heart, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); harzianopyridone was added therein; further the complex II was added thereto; then potassium succinate with final concentration of 10 mM was added; and the reaction was started at 25° C. Reaction rate was measured by that the formation rate of reduced form of DCIP (àmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 11

Inhibitory Activity of Harzianopyridone on Rat Liver Complex II

With regard to the complex II of the rat liver, mitochondria prepared according to the same method described in the referential example 1 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); harzianopyridone was added therein; further the complex II was added thereto; then potassium succinate with final concentration of 10 mM was added; and the reaction was started at 25° C. Reaction rate was measured by that the formation rate of reduced form of DCIP (àmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

EXAMPLE 12

Inhibitory Activity of Harzianopyridone on *Ascaris suum* Complex II

With regard to the complex II of the *Ascaris suum*, the purified complex II prepared according to the same method of example 3 was used. Succinate dehydrogenase activity of the complex II was measured by changes of maximum absorption, which was specific to the electron acceptor (DCIP), from oxidized form of DCIP to reduced form with the addition of succinate. Namely, ubiquinone-2 and DCIP were added to the level of 100 ìM and 70 ìM, respectively, into 50 mM phosphate buffer (pH 7.5); harzianopyridone was added therein; further the complex II was added thereto; then potassium succinate with final concentration of 10 mM was added; and the reaction was started at 25° C. Reaction rate was measured by that the formation rate of reduced form of DCIP (àmM$^{-1}$ 1 cm$^{-1}$: 21) which accepted electron from succinate was measured at absorption changes of 600 nm. Activity was indicated by molar numbers of DCIP reduced per minute. Potassium cyanide, final concentration of 10 mM, was added due to necessity for prevention of leakage of reduction activity by inhibiting terminal oxidase. Result is as shown in Table 2.

Inhibitory activities obtained in referential examples and examples hereinabove are as shown in Table 2, and 50% inhibitory concentration of the complex II (IC$_{50}$, nM) is shown.

TABLE 2

| Inhibitor | complex II | | |
|---|---|---|---|
| | Bovine heart | Rat liver | Ascaris suum |
| Atpenin A4 | 11 | 24 | 220 |
| Atpenin A5 | 3.6 | 3.7 | 32 |
| Atpenin B | 10 | 20 | 50 |
| Harzianopyridone | 17 | 200 | 2,000 |
| Thenoyltrifluoro Aceton | 5,800 | NT | NT |
| Carboxin | 1,100 | NT | NT |

NT: not tested

From the above result of measurement, atpenins A4, A5, B and harzianopyridone, which are 2-pyridinole derivatives or the tautomers thereof, i.e. 2-pyridone derivatives, showed strong inhibitory activities with nM order against bovine heart complex II, rat liver complex II and *Ascaris suum* complex II. Comparing inhibitory activities against the bovine heart complex II with the prior known complex II inhibitors such as thenoyltrifluoroacetone and carboxin, atpenin A4, A5, B and harzianopyridone of the present invention showed 60-1600 times stronger inhibitory activities.

INDUSTRIAL APPLICABILITY

As explained hereinabove, atpenins A4, A5, B and harzianopyridone, which are 2-pyridinole derivatives or their tautomers, 2-pyridone derivatives, or salt thereof, inhibited the bovine heart complex II, rat liver complex II and *Ascaris suum* complex II with strong activities of nM order levels. Consequently, 2-pyridinol derivatives or the tautomers thereof, i.e. 2-pyridone derivatives, are expected to be useful as inhibitors against the electron transport system complex II.

What is claimed is:

1. An electron transport system complex II inhibitor comprising:
    an effective amount of a purified 2-pyridinol compound, or salt thereof, as an active ingredient, to inhibit electron transport system complex II in mitochondria, wherein, the effective amount is 3.6 nM to 220 nM as a 50% inhibitory concentration, and
    the 2-pyridinol compound is selected from the group consisting of:
    atpenin A4 represented by the formula [III]

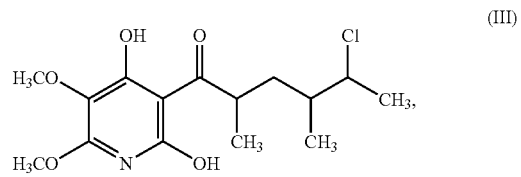

atpenin A5 represented by the formula [IV]

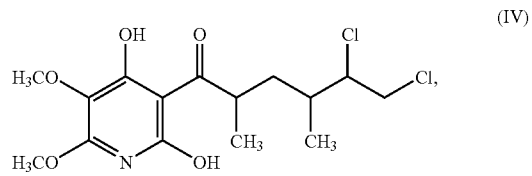

and
    atpenin B represented by the formula [VI]

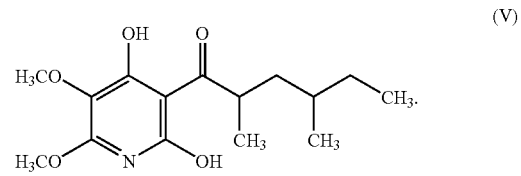

2. The electron transport system complex II inhibitor according to claim 1, wherein the active ingredient is atpenin A4 represented by the formula [III], and the atpenin A4 has inhibitory activity against bovine heart complex II.

3. The electron transport system complex II inhibitor according to claim 1, wherein the active ingredient is atpenin A4 represented by the formula [III], and the atpenin A4 has inhibitory activity against rat liver complex II.

4. The electron transport system complex II inhibitor according to claim 1, wherein the active ingredient is atpenin A4 represented by the formula [III], and the atpenin A4 has inhibitory activity against *Ascaris suum* complex II.

5. The electron transport system complex II inhibitor according to claim 1, wherein the active ingredient is atpenin A5 represented by the formula [IV], and the atpenin A5 has inhibitory activity against bovine heart complex II.

6. The electron transport system complex II inhibitor according to claim 1, wherein the active ingredient is atpenin A5 represented by the formula [IV], and the atpenin A5 has inhibitory activity against rat liver complex II.

7. The electron transport system complex II inhibitor according to claim 1, wherein the active ingredient is atpenin A5 represented by the formula [IV], and the atpenin A5 has inhibitory activity against *Ascaris suum* complex II.

8. The electron transport system complex II inhibitor according to claim 1, wherein the active ingredient is atpenin B represented by the formula [VI], and the atpenin B has inhibitory activity against bovine heart complex II.

9. The electron transport system complex II inhibitor according to claim 1, wherein the active ingredient is atpenin B represented by the formula [V], and the atpenin B has inhibitory activity against rat liver complex II.

10. The electron transport system complex II inhibitor according to claim 1, wherein the active ingredient is atpenin B represented by the formula [V], and the atpenin B has inhibitory activity against *Ascaris suum* complex II.

* * * * *